United States Patent [19]

Erhardt et al.

[11] 4,450,173
[45] May 22, 1984

[54] COMPOUNDS AND METHOD FOR TREATMENT OR PROPHYLAXIS OF CARDIAC DISORDERS

[75] Inventors: Paul W. Erhardt; Robert J. Borgman, both of Mundelein, Ill.

[73] Assignee: American Hospital Supply Corporation, Evanston, Ill.

[21] Appl. No.: 390,629

[22] Filed: Jun. 21, 1982

Related U.S. Application Data

[63] Continuation of Ser. No. 211,340, Nov. 28, 1980, abandoned.

[51] Int. Cl.$^3$ .................... A61K 31/24; C07C 101/42
[52] U.S. Cl. .................................. 424/309; 424/304; 424/319; 560/21; 560/22; 560/39; 560/40; 560/44; 562/451; 562/452; 562/434; 562/435; 260/465 D; 260/501.17; 260/501.19; 260/501.18
[58] Field of Search .................... 560/39, 40, 44, 21, 560/22; 424/309, 319, 304; 562/451, 452; 260/465 D, 501.17, 501.18, 501.19

[56] References Cited

U.S. PATENT DOCUMENTS

| | | | |
|---|---|---|---|
| 3,793,365 | 2/1974 | Winter et al. | 562/427 |
| 4,146,638 | 3/1979 | Renth et al. | 562/451 |
| 4,183,954 | 1/1980 | Bertelli | 562/451 |
| 4,191,765 | 3/1980 | Fritsch et al. | 562/451 |
| 4,220,659 | 9/1980 | Koppe et al. | 562/451 |
| 4,241,171 | 12/1980 | Singh et al. | 564/349 |
| 4,241,177 | 12/1980 | Singh et al. | 562/452 |

Primary Examiner—James H. Reamer
Attorney, Agent, or Firm—Bernard, Rothwell & Brown

[57] ABSTRACT

A short-acting β-blocking compound of the formula

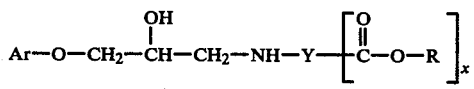

wherein Ar may be substituted or unsubstituted aromatic, Y may be a straight or branched carbon chain or aralkyl, R may be lower alkyl, lower alkenyl, lower alkynyl, aryl or aralkyl, and x is an integer from 1 to about 3; or a pharmaceutically acceptable salt thereof.

20 Claims, No Drawings

COMPOUNDS AND METHOD FOR TREATMENT OR PROPHYLAXIS OF CARDIAC DISORDERS

This is a continuation of application Ser. No. 211,340, filed Nov. 28, 1980, now abandoned.

BACKGROUND OF THE INVENTION

The present invention relates to the treatment or prophylaxis of cardiac disorders. More particularly, the invention relates to a novel method of treatment or prophylaxis of cardiac disorders which comprises administration of β-adrenergic blocking agents and to compounds useful in such method.

The therapeutic and prophylactic uses of compounds which block sympathetic nervous stimulation of β-adrenergic receptors in the heart, lungs, vascular system and other organs are well documented. Typically, such compounds are administered therapeutically to patients suffering from ischemic heart disease or myocardial infarction for the purpose of reducing heart work, i.e., heart rate and contractile force. Reducing heart work reduces oxygen demand, and may also actually increase oxygen supply. Thus reducing heart work can aid in the prevention of further tissue damage and can relieve angina pectoris.

β-Adrenergic stimulation may also aggravate or cause arrhythmias because of increased levels of catecholamines. Thus β-blocking agents may be employed to reduce the risks of arrhythmias.

Compounds have been discovered which selectively block β-adrenergic receptors in various organs. Beta receptors in the heart are generally referred to as $\beta_1$ receptors, and those associated with vasodilation and bronchodilation are $\beta_2$ receptors. Non-selective β-blockers are not preferred for the treatment of cardiac disorders because of their hypertensive action and potential undesirable effects on asthmatic patients. A number of $\beta_1$ selective adrenergic blocking agents have been discovered. Smith, L. H., J. Appl. Chem. Biotechnol., 28, 201–212 (1978). Most of such compounds are structural variations of 1-amino-3-aryloxy-2-propanol.

Heretofore, the emphasis in β-blocker research has been to develop compounds which can be administered to cardiac patients over long periods of time. However, often it is desirable in the critical care setting to quickly reduce heart work or improve rhythmicity during a cardiac crisis, e.g., during or shortly after a myocardial infarction. Conventional β-blocking agents can be employed for such treatment, but their duration of action may be much longer than desired by the physician. A β-blocking agent possessing a long duration of action does not allow precise control of heart work or prompt reversal of the β-blocking effect, which may be required in a critical care setting. For instance, if heart output becomes dangerously low, it is desirable to quickly reduce or eliminate β-blocking activity. The lingering activity of available β-blocking agents can be counterproductive and can greatly complicate the therapeutic decisions required of the physician during such critical care of cardiac patients.

SUMMARY OF THE INVENTION

In accordance with the present invention, disclosed herein is a method for the treatment or prophylaxis of cardiac disorders in a mammal comprising administering to such mammal a short-acting compound of the formula:

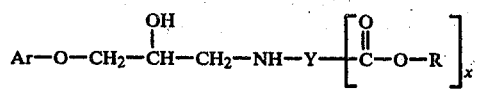

wherein Y is a straight or branched carbon chain of from 1 to about 10 carbon atoms or aralkyl of from 8 to about 20 carbon atoms; R is lower alkyl, lower alkenyl, lower alkynyl, aryl or aralkyl; x is an integer from 1 to about 3; Ar is unsubstituted aromatic or aromatic substituted with lower alkyl, lower alkenyl, lower alkynyl, lower alkoxy, halogen, acetamido, amino, nitro, lower alkylamino, hydroxy, lower hydroxyalkyl, cyano, or a group of the formula

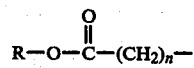

wherein n is an integer from 0 to about 10; or a pharmaceutically acceptable salt thereof.

DETAILED DESCRIPTION OF THE INVENTION

In accordance with the present invention, it has been discovered that compounds having an ester function in external amine substituents possess β-adrenergic blocking activity and have a short duration of action. Such compounds may also contain more than one ester group in the same molecule. The compounds of the present invention are represented by the formula:

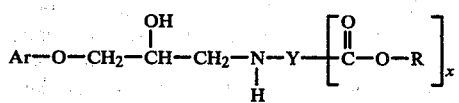

Y may be a straight or branched carbon chain of from 1 to about 10 carbon atoms, e.g., methylene, ethylene, propylene, 2-ethylhexylene, 1,1-dimethylethylene, and the like or aralkyl of from 8 to about 20 carbon atoms, such as dialkylene phenyl, e.g., 4-ethylenebenzyl, 1-propylene-(4-naphthyl)-2-n-butyl, and the like.

R may be lower alkyl of from 1 to about 10 carbon atoms, such as methyl, propyl, t-butyl, 3-propylheptyl, and the like; lower alkenyl of from 2 to about 10 carbon atoms, such as ethenyl, propenyl, 4-ethyl-2-hexenyl, and the like, lower alkynyl of from 2 to about 10 carbon atoms, such as ethynyl, propynyl, 4-ethyl-3-octynyl, and the like; aryl of from 6 to about 10 carbon atoms such as phenyl, 2-tolyl, 2-methoxyphenyl, naphthyl, and the like or aralkyl, wherein the alkyl portion contains from 1 to about 10 carbon atoms and the aryl portion contains from 6 to about 10 carbon atoms, such as benzyl, phenethyl, 1-naphthylpropyl, 3,4-dimethoxyphenethyl, and the like.

The amine substituent may contain one or more ester groups, thus x is an integer from 1 to about 3 provided that when x is greater than 1, different occurrances of the —COOR group may be the same or different.

Ar represents substituted or unsubstituted aromatic, including monocyclic, polycyclic, and heterocyclic ring systems. Aromatic substituents include lower alkyl, of from 1 to about 10 carbon atoms, lower alkenyl, of from 2 to about 10 carbon atoms, lower alkynyl, of from 2 to about 10 carbon atoms, lower alkoxy of from 1 to about about 10 carbon atoms, halogen, acetamido, amino, nitro, lower alkylamino, of from 1 to about 10 carbon atoms, hydroxy, lower hydroxyalkyl of from 1 to about 10 carbon atoms, cyano, or a group of the formula $$R-O-\overset{\overset{O}{\|}}{C}-(CH_2)_n-$$

wherein n is an integer from 0 to about 10. When two or more groups of the same designation occur in the same formula, those groups are not necessarily identical. The compounds described herein are not limited to any particular stereoisomeric configuration.

In preferred compounds, Y is a straight or branched carbon chain of from 1 to about 6 carbon atoms or aralkyl of from 8 to about 12 carbon atoms. Most preferably, Y is a straight or branched carbon chain of from 1 to about 4 carbon atoms. R is preferably lower alkyl of from 1 to about 5 carbon atoms, lower alkenyl of from 2 to about 5 carbon atoms, lower alkynyl of from 2 to about 5 carbon atoms, aryl of from 6 to about 8 carbon atoms, or aralkyl, wherein the alkyl portion contains from 1 to about 5 carbon atoms and the aryl portion contains from 6 to about 10 carbon atoms. Most preferably, R is lower alkyl of from 1 to about 4 carbon atoms or aralkyl, wherein the alkyl portion contains from 1 to about 4 carbon atoms and the aryl portion contains from 6 to about 8 carbon atoms. Particularly preferred R groups are methyl and ethyl. The integer x is preferably 1 or 2; most preferably 1.

Ar is preferably unsubstituted aromatic or aromatic substituted with lower alkyl of from 1 to about 5 carbon atoms, lower alkenyl of from 2 to about 5 carbon atoms, lower alkynyl of from 2 to about 5 carbon atoms, lower alkoxy of from 1 to about 5 carbon atoms, fluoro, chloro, acetamido, amino, nitro, lower alkylamino of from 1 to about 5 carbon atoms, hydroxy, lower hydroxyalkyl of from 1 to about 5 carbon atoms, cyano, or a group of the formula $$R-O-\overset{\overset{O}{\|}}{C}-(CH_2)_n-$$

wherein n is an integer from 0 to about 5. Ar is more preferably unsubstituted phenyl or phenyl substituted with lower alkyl of from 1 to about 5 carbon atoms, fluoro, chloro, nitro or a group of the formula $$R-O-\overset{\overset{O}{\|}}{C}-(CH_2)_n-$$

wherein n is an integer of from 1 to about 5 and R is lower alkyl of from 1 to about 5 carbon atoms. Most preferably, Ar is 2-alkylphenyl, eg. 2-methylphenyl.

The compounds of this invention may be administered as their pharmaceutically acceptable acid addition salts, e.g., as the hydrochloride, sulfate, phosphate, gluconate, tartrate, etc.

The compounds of the present invention may be prepared by a number of reaction procedures. The following four reaction schemes have been employed. In all of the reaction schemes, an aryl ether epoxide is used as the starting material. The aryl ether epoxide is prepared from an appropriately derivatized aryl hydroxy compound as follows:

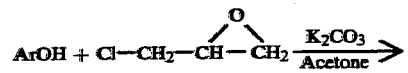

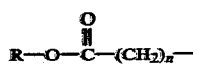

The aryl ether epoxide may then be reacted in the following manner to provide the desired product:

Scheme I

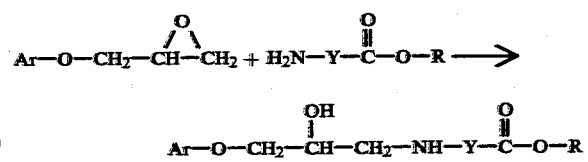

Scheme II

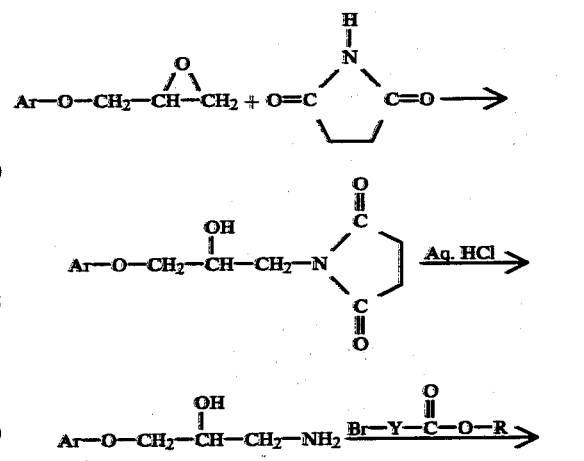

Scheme III

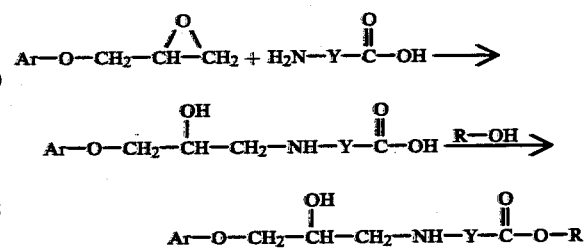

Scheme IV

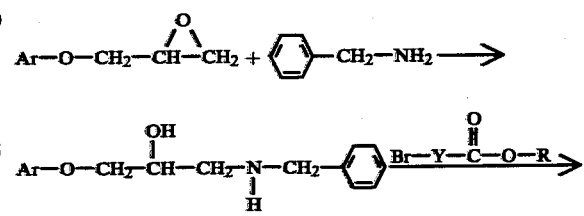

-continued

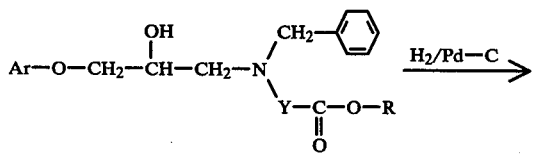

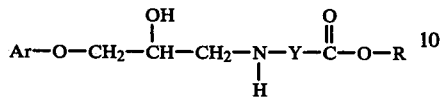

The compounds of this invention are advantageously administered parenterally, e.g., by intravenous injection or intravenous infusion. Formulations for intravenous injection preferably include the active compound as a soluble acid addition salt in a properly buffered isotonic solution.

The dosage administered to a patient and the duration of infusion will depend upon the patient's needs and the particular compounds employed. For short periods of infusion, e.g., less than about three hours, the duration of effect is thought to be determined by both metabolic effects and distribution phenomena. For relatively long periods of infusion, e.g., greater than about three hours, the duration of effect is thought to depend largely on metabolic effects. Accordingly, although the present methods and compounds are generally useful for short term infusion therapy, certain compounds are preferred for longer durations of infusion. This principle is demonstrated by reference to the 40 minute and three hour infusion studies described in Examples LX-LXXIV. The compounds have been found to be generally non-toxic within conventional dosage ranges. Dosages of from about 0.001 to about 100 mg. per kg. of body weight per hour are generally employed, with preferred dosages ranging from about B 0.01 to about 10 mg. per kg. of body weight per hour.

The compounds of the present invention have a relatively short duration of action compared to conventional β-blockers. In vitro studies in human whole blood indicate that the ester functions are subject to enzymatic cleavage. Compounds of the present invention in which the aromatic portion, Ar, is also substituted with an ester-containing group, have two or more potentially labile sites for enzymatic hydrolysis. Thus the β-blocking activity can be carefully controlled by regulating dosage size and rate of administration. The time required for substantially complete disappearance of the β-blocking effects of the compounds of the present invention ranges from about 5–10 minutes to about 1 hour or more. Generally, it is preferred that the recovery is accomplished within about 10–15 minutes. A short acting β-blocker can advantageously be infused at a rate sufficient to provide the desired action, e.g., titrated to the specific patient's needs, and such action can be promptly discontinued by stopping the infusion. Thus, the method of the present invention provides a very useful therapeutic alternative in the treatment or prophylaxis of cardiac disorders.

The present invention is further illustrated by the following examples which are not intended to be limiting.

EXAMPLE I

This example describes procedures producing the following compound:

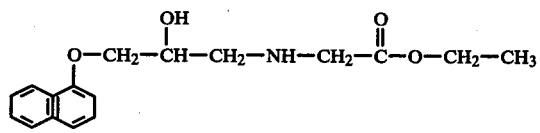

2,3-Epoxypropoxybenzene

A mixture of 9.4 gm (0.1 mole) of phenol, 28 gm (0.2 mole) of potassium carbonate and 30 mL (0.4 mole) of epichlorohydrin in 250 mL acetone was heated to reflux for 12 hours. The reaction medium was then filtered and evaporated leaving an oil which was taken up in toluene and successively washed with 100 mL water, 2×100 mL 1.0 N sodium hydroxide and 2×100 mL water. The toluene phase was dried with magnesium sulfate and evaporated to provide a clear oil which was chromatographed on a Prep-500 silica gel column employing hexane: ethyl acetate (9:1) as the mobile phase. Collection of the major peak and evaporation of solvent provided 9 gm (60%) of a clear oil whose NMR and IR spectra were consistent with the assigned structure.

Ethyl N-(2-Hydroxy-3-phenoxypropyl) glycinate Oxalate

A solution of 20 gm (0.14 mole) of glycine ethyl ester hydrochloride and 40 gm $K_2CO_3$ in 100 mL of water was extracted with ether (5×100 mL). The ethereal phase was then dried with $Na_2SO_4$ and evaporated under reduced pressure at a temperature not exceeding 40° C. to provide 10.5 gm (71%) of glycine ethyl ester free amine. The glycine ethyl ester free amine (0.10 mole) was used immediately by reacting with 4.0 gm (0.03 mole) of 2,3-epoxypropoxybenzene in refluxing ethanol (50 mL). After 4 hours the reaction medium was evaporated under reduced pressure and the resulting oil taken up in 50 mL toluene and washed with 4×50 mL water. The organic phase was dried with $MgSO_4$ and evaporated to a yellow oil. An analytical sample of the free amine was obtained by crystallization from ethyl acetate: mp 49°–50°. The elemental analysis of this product was consistent with the formula, $C_{13}H_{19}NO_4$. The major portion of this oil was converted to its oxalate salt and crystalled from ethanol-ether to provide 0.8 gm (8%): mp 144°–145° C. The NMR and IR spectra and elemental analyses conformed to the assigned structure.

EXAMPLE II

This example describes the procedures for producing a compound of the formula

1-Naphthyl-2,3-epoxypropyl Ether

The experiment of Example I for preparing 2,3-epoxypropoxybenzene was repeated in all essential details, except that 1-naphthol was substituted for phenol, and the final product was isolated by vacuum distillation: bp 112°–114° C. (p=0.25 mm Hg). The NMR and IR spectra and elemental analyses conformed to the assigned structure.

Ethyl N-[[2-Hydroxy-3-(1-naphthoxy]propyl]glycinate Oxalate Hemihydrate

A mixture of 4.0 gm (0.02 mole) of 1-(2,3-epoxypropoxy)naphthalene, 5.6 gm (0.04 mole) of glycine ethyl ester hydrochloride and 5.5 mL (0.04 mole) triethylamine in 50 mL of ethanol was heated to reflux for 2 hours. The reaction medium was then evaporated under reduced pressure and the resulting oil taken up in 50 mL toluene and washed with 2×50 mL water. The organic phase was dried over MgSO₄ and evaporated under reduced pressure. The resulting oil was crystallized as its oxalate salt from water and provided 1.1 gm (14%) of product: mp 161°-162° C. The NMR spectrum was consistent with the assigned structure, and the elemental analysis was consistent with the formula $C_{19}H_{23}NO_8 \cdot \frac{1}{2}H_2O$. An anhydrous analytical sample was also obtained by crystallization from acetone: mp 169°-170° C. The NMR spectrum of the analytical sample was also consistent with the assigned structure, and the elemental analysis was consistent with the formula $C_{19}H_{23}NO_8$.

EXAMPLE III

This example describes procedures for producing the following compound:

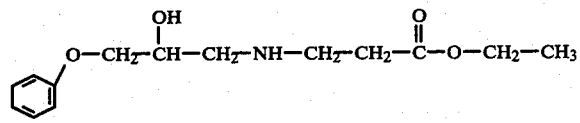

1-Succinimido-3-phenoxy-2-propanol

A mixture of 15 gm (0.1 mole) of 2,3-epoxypropoxybenzene (prepared as described in Example I) and 9.9 gm (0.1 mole) of succinimide in 100 mL ethanol having 10 drops of pyridine was heated to reflux for 4 hours. After standing 24 hours at room temperature a white crystalline product separated. This material was collected, air-dried and recrystallized from 700 mL ethyl acetate:hexane (6:1) to give 18 gm (72%) of white crystals: mp 130°. The NMR spectrum and the elemental analyses were consistent with the assigned structure.

1-Amino-3-phenoxy-2-propanol Hydrochloride

1-Succinimido-3-phenoxy-2-propanol (16 gm, 0.06 mole) was dissolved in 100 mL conc. HCl and 100 mL ethanol and heated to reflux for 6 hours. After the reaction, the mixture was evaporated to a white residue which was then taken up in 25 mL water and washed with 3×50 mL ether. The aqueous phase was then evaporated and the white-residue recrystallized from ethanol to provide 8.3 gm (69%) of white crystals: mp 226°-228°. The NMR spectrum was consistent with the assigned structure and the elemental analysis was consistent with the molecular formula $C_9H_{14}NO_2Cl$.

Ethyl 3-[N-[2-Hydroxy-3-phenoxy)propyl]amino]propionate Oxalate

A mixture of 3.4 gm (0.02 mole) of 1-amino-3-phenoxy-2-propanol hydrochloride, 2.6 mL (0.02 mole) of ethyl 3-bromopropionate and 2.8 mL (0.02 mole) of triethylamine in 20 mL of ethanol was heated to reflux for 12 hours. The reaction medium was then filtered and evaporated and the residue taken up in 25 mL water/50 mL ether. The phases were separated and the ether phase washed twice with 25 mL water. The ethereal phase was then dried with magnesium sulfate and evaporated to provide 1.86 gm of a clear oil. A 1.65 gm (0.0062 mole) portion of this oil in 5 mL ethanol was then added to 0.78 gm (0.0062 mole) of oxalic acid dihydrate in 15 mL ethanol and after standing at room temperature the oxalate salt was produced as a crystalline solid. This material was recrystallized from acetone to provide 1.1 gm (16%) white crystals: mp 137°-138°. The NMR spectrum was consistent with the assigned structure and the elemental analysis was consistent with the molecular formula $C_{16}H_{23}NO_8$.

EXAMPLE IV

This example describes a procedure for preparing a compound of the formula

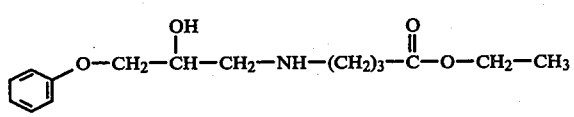

Ethyl 4-[N-[(2-Hydroxy-3-phenoxy)propyl]aminobutyrate

A mixture of 10 gm (0.10 mole) of 4-aminobutyric acid, 6.6 mL of 2,3-epoxypropoxybenzene (0.05 mole) (prepared as described in Example I) and 4.0 gm (0.10 mole) of NaOH in 160 mL aqueous dioxane (1:3) was heated to reflux for 4 hours. After cooling, 100 mL of water was added and the aqueous medium washed with 400 mL ether. The aqueous phase was acidified to pH 1 by adding concentrated HCl and then evaporated to a semi-solid residue which was extracted with ethyl acetate. This process removed 5.3 gm (95%) of NaCl side product. Evaporation of ethyl acetate provided the crude amino acid product as an oil which was immediately esterified with 500 mL ethanol utilizing a Soxhlet Extractor charged with 250 gm of activated 3A molecular sieves and employing a 96-hour reaction time. Concentration of the ethanol and treatment with ether provided a crystalline material which was subsequently recrystallized from ethyl acetate to provide 4.1 gm (25%) of product: mp 109°-110° C. The NMR spectrum was consistent with the assigned structure, and the elemental analysis was consistent with the formula $C_{15}H_{24}NO_4Cl$.

EXAMPLE V

This example describes the experimental procedures for producing the following compound:

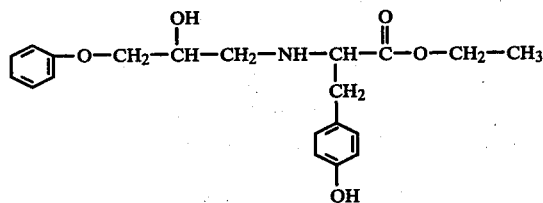

Ethyl N[(2-Hydroxy-3-phenoxy)propyl]tyrosinate

A mixture of 1.4 mL (0.01 mole) of 2,3-epoxypropoxybenzene (prepared as described in Example I) and 2.1 gm (0.01 mole) of tyrosine in 10 mL ethanol was heated to reflux for 4 hours. After the reaction, the mixture was evaporated to a thick clear oil which was then dissolved in 50 mL toluene and partitioned with 2×40 mL water. The organic phase was then dried with magnesium sulfate and evaporated to an oil. This oil was taken up in 15 mL of ethanolic HCl and treated with 175 mL ether. An oil was gradually produced from this solution after cooling. This oil was taken up in ethyl acetate and upon evaporation of this solvent, an amorphous solid was obtained: 0.5 gm (14%); mp 60°-70°. The NMR spectrum was consistent with the assigned structure and the elemental analysis was consistent with the molecular formula $C_{20}H_{26}NO_5Cl$.

EXAMPLE VI

This example describes a procedure for preparing a a compound of the formula

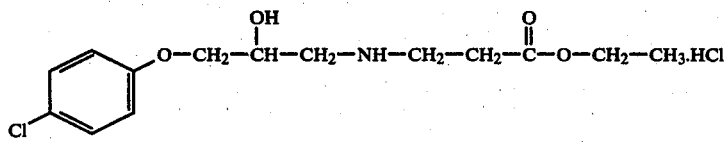

Ethyl 3[N-[3-[4-(chlorophenoxy)-2-hydroxy]propyl]amino]-propionate Hydrochloride A solution of 9.2 gm (50 mmol) of 4-chloro-1-(2,3-epoxypropoxy)benzene and 5.5 mL (50 mmol) of benzylamine in 125 mL of ethanol was heated to reflux for 4 hours (a 10 mL aliquot was then treated with concentrated HCl and ether to provide an analytical sample of the intermediate secondary benzylamine hydrochloride as a white crystalline product: mp 169°-170° C.). After cooling the reaction mixture, 6 mL (47 mmol) of ethyl 3-bromopropionate and 6.5 mL (47 mmol) of triethylamine were added and the mixture heated to reflux for another 10 hours. The reaction medium was then evaporated and the residue taken up in 50 mL toluene—50 mL water. The organic phase was washed an additional two times with 50 mL portions of water and then dried over $MgSO_4$ and evaporated to provide the Ethyl 3-[N-benzyl-N-[3-[(4-chlorophenoxy)-2-hydroxy]propyl-]amino]propionate intermediate as an oil which was characterized by NMR spectroscopy. This oil was used directly in the next reaction by redissolving it in 100 mL of ethanol, adding 7 mL (100 mmol) of acetyl chloride, 100 mg of 10% Pd-C and hydrogenating under 50 psi for 20 minutes. The reaction medium was then filtered and evaporated under reduced pressure to provide the product as an oil which yielded 6.5 gm (41% overall yield) of white crystals from ethanol-ether: mp 119°-120° C. The NMR spectrum and elemental analysis were consistent with the assigned structure.

EXAMPLE VII

This example describes procedures for preparing a compound of the formula

Methyl 3(4-Hydroxyphenyl)propionate

A solution of 300 gm (1.81 mole) of 3-(4-hydroxyphenyl) propionic acid in 1 liter of anhydrous methanol containing 10 drops of concentrated $H_2SO_4$ was heated to reflux for 72 hours in a Soxhlet Extractor charged with 200 gm of 3A molecular sieves (Linde 3A, 1/16 pellets). The reaction medium was then evaporated under reduced pressure and the resulting oil taken up in 750 mL of toluene and washed with three 500 mL portions of water. The toluene phase was then dried with $MgSO_4$ and evaporated under reduced pressure to provide 228.4 gm (70%) of a clear oil which was characterized by NMR spectroscopy and utilized directly in the next step without additional purification.

Methyl 3[4-(2,3-Epoxypropoxy)phenyl]propionate

A mixture of 228 gm (1.27 mole) of methyl 3-(4-hydroxyphenyl)propionate, 263 gm (1.90 mole) of $K_2CO_3$ and 298 mL (3.80 mole) of epichlorohydrin in 2 liters of acetone was stirred and heated to reflux for 20 hours. The reaction medium was then filtered and evaporated under reduced pressure. The resulting oil was taken up in 1 liter of toluene and washed consecutively with 500 mL water, 2×500 mL 1N NaOH and 2×500 mL water. The toluene phase was then dried over $MgSO_4$ and evaporated under reduced pressure to provide a clear oil which was further purified by vacuum distillation. The final yield of purified oil was 131.2 gm (44%): bp 156° (p=0.4 mm Hg). The NMR and IR spectra of the product were consistent with the assigned structure and the elemental analysis was consistent with the formula $C_{13}H_{16}O_4$.

Ethyl 3-[N-[2-Hydroxy-3-[4-[2-(methoxycarbonyl)ethyl]-phenoxy]propyl]amino]propionate Hydrochloride A mixture of 5 gm (0.02 mole of methyl 3-[4-(2,3-epoxypropoxy)phenyl]propionate, 3 gm (0.02 mole) of ethyl 3-aminopropionate hydrochloride and 2.8 ml (0.02 mole) of triethylamine in 25 mL of isopropanol was heated to reflux for 4 hours. The reaction medium was then cooled and the triethylamine hydrochloride sideproduct which crystallized was removed by filtration. The mother liquor was then evaporated under reduced pressure and the resulting residue taken up in ethanol and treated with ethereal HCl to provide 1 gm (12%) as a crystalline solid: mp 110°-111°. The NMR spectrum was consistent with the assigned structure and the elemental analysis was consistent with the formula $C_{18}H_{28}NO_6Cl$.

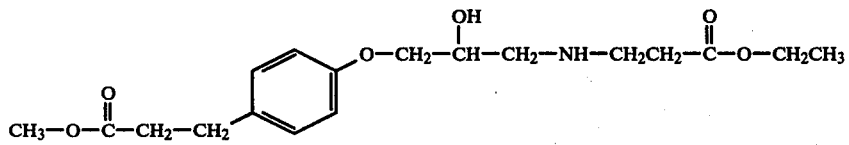

EXAMPLE VIII

This example describes procedures for the preparation of a compound of the formula

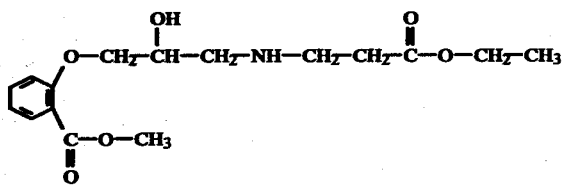

Methyl 2-(2,3-Epoxypropoxy)benzoate

The procedure of Example VII for producing methyl 3-[4-(2,3-epoxypropoxy)phenyl]propionate was repeated in all essential details, except methyl salicylate was substituted for methyl 3-(4-hydroxyphenyl)propionate. The boiling point of the product was 148° (p=75μ). The NMR spectrum was consistent with the assigned structure and the elemental analysis with the formula $C_{11}H_{12}O_4$.

Ethyl 3-[N-[2-Hydroxy-3-[2-(methoxycarbonyl)phenoxy]-propyl]amino]propionate Oxalate Hemihydrate The procedure for Example VII for producing ethyl 3-[N-[2-hydroxy-3-[4-[2-(methoxycarbonyl)ethyl]-phenoxy]propyl]amino]propionate hydrochloride was repeated in all essential details except methyl 2-(2,3-epoxypropoxy) benzoate was substituted for 3[4-(2,3-epoxypropoxy)phenyl]propionate and the product was crystallized as its oxalate salt from 2-propanol ether and then recrystallized from acetone. Approximately 2 gm (25%) of product was obtained having a melting point of 90°–91° C. The NMR spectrum was consistent with the assigned structure and the elemental analysis was consistent with the formula $C_{18}H_{25}NO_{10} \cdot \frac{1}{2}H_2O$.

EXAMPLE IX

This example describes the preparation of 1-(2,3-epoxypropoxy)-2-methylbenzene, which may be used as a starting material for certain compounds described herein. The procedure is representative and may be modified to provide starting material for a variety of compounds. A mixture of 52 mL (0.5 mole) of ortho-cresol, 103 gm (0.75 mole) of $K_2CO_3$ and 117 mL (1.5 mole) of epichlorohydrin in 600 mL of acetone was heated to reflux for 16 hours. The reaction medium was then filtered and evaporated under reduced pressure. The resulting oil was taken up in 400 mL of toluene and washed consecutively with 200 mL of water, 2×200 mL of 1.0N aq. sodium hydroxide and 200 mL of water. The organic phase was then dried over $MgSO_4$ and evaporated under reduced pressure. The resulting oil, 54 gm (65%), was utilzied directly in the next step without additional purification. The product was characterized by NMR spectroscopy, and the spectrum was consistent with the assigned structure.

EXAMPLES X–XX

These examples describe the preparation of compounds identified in Table I. The compounds were prepared utilizing the procedure of Example VI in all essential details, except 1-(2,3-epoxypropoxy)-2-methylbenzene was substituted for 4-chloro-1-(2,3-epoxypropoxy)benzene and the appropriate bromocarboxylic acid ester was subjected for ethyl 3-bromopropionate. Each of the compounds was characterized by NMR spectroscopy and elemental analysis.

TABLE I

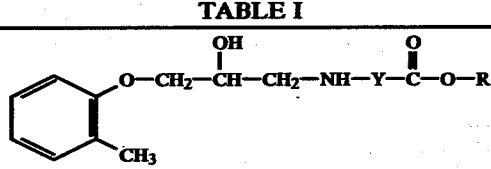

| Example | Y | R | Salt | Melting Point | Yield (%) |
|---|---|---|---|---|---|
| X | —CH₂—CH₂— | —CH₂CH₃ | HCl | 82–84° C. | 44 |
| XI | —(CH₂)₃— | —CH₂CH₃ | HCl | 77–78° C. | 16 |
| XII | —(CH₂)₄— | —CH₂CH₃ | HCL | 102–103° C. | 46 |
| XIII | phenyl | —CH₂CH₃ | Free Amine | 102–103° C. | 20 |
| XIV | phenyl (with CH₃) | —CH₂CH₃ | Oxalate | 89–92° C. | 18 |
| XV | —CH₂—phenyl | —CH₂CH₃ | HCl | 144–145° C. | 15 |
| XVI | —CH₂—phenyl | —CH₃ | HCl | 179–180° C. | 12 |

TABLE I-continued

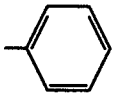

| Example | Y | R | Salt | Melting Point | Yield (%) |
|---|---|---|---|---|---|
| XVII | —CH₂—CH₂— | —CH₃ | Oxalate | 152–153° C. | 10 |
| XVIII | —CH₂—CH₂— | 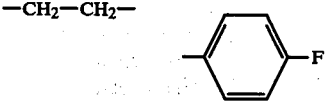 | HCl | 148–149° C. | 16 |
| XIX | —CH₂—CH₂— | 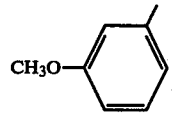 | HCl | 142–144° C. | 14 |
| XX | —CH₂—CH₂ | —CH₂CF₃ | Hemi-Oxalate | 133–134° C. | 5 |

EXAMPLES XXI–XXVI

These examples describe the preparation of the compounds identified in Table II. The compounds were prepared utilizing the procedure of Example VI in all essential details, except the appropriate 2,3-epoxypropoxyaryl compound was substituted for 4-chloro-(2,3-epoxypropoxy)benzene. Each of the compounds was characterized by NMR spectroscopy and elemental analysis.

TABLE II

Ar—O—CH₂—CH(OH)—CH₂CH₂—NH—CH₂—CH₂—C(=O)—O—CH₂CH₃

| Example | Ar | Salt | Melting Point | Yield % |
|---|---|---|---|---|
| XXI | 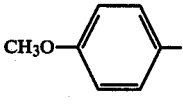 | Oxalate | 134–137° C. | 15 |
| XXII | 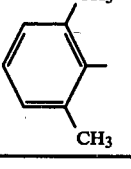 | HCl | 94–95° C. | 21 |
| XXIII | 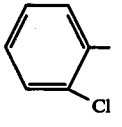 | Oxalate | 127–128° C. | 18 |

TABLE II-continued

Ar—O—CH₂—CH(OH)—CH₂CH₂—NH—CH₂—CH₂—C(=O)—O—CH₂CH₃

| Example | Ar | Salt | Melting Point | Yield % |
|---|---|---|---|---|
| XXIV | 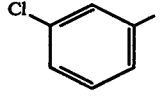 | Oxalate | 129–132° C. | 22 |
| XXV | 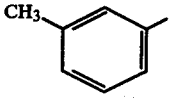 | HCl | 117–119° C. | 20 |
| XXVI |  | Hemi-Oxalate | 148–149° C. | 5 |

EXAMPLE XXVII–XXVIII

These examples describe the preparation of the compounds identified in Table III. The compounds were prepared utilizing the procedure of Example III in all essential details, except the appropriate bromocarboxylic acid ester was substituted for ethyl 3-bromopropionate, and 1-(2,3-epoxypropoxy)2-methylbenzene was substituted for 2,3-epoxypropoxybenzene. The compounds were identified by NMR spectroscopy and elemental analysis.

TABLE III

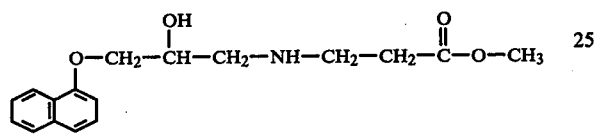

| Example | Y | R | Melting Point | Salt | Yield (%) |
|---|---|---|---|---|---|
| XXVII | —CH₂— | —CH₂CH₃ | 137–138° C. | Oxalate | 14 |
| XXVIII | —CH₂CH₂— | —(CH₂)—⟨cyclohexyl with OCH₃, OCH₃⟩ | 125–129° C. | Hemi-Oxalate | 23 |

EXAMPLE XXIX

The procedure of Example IV was repeated in all essential details to produce a compound of the formula

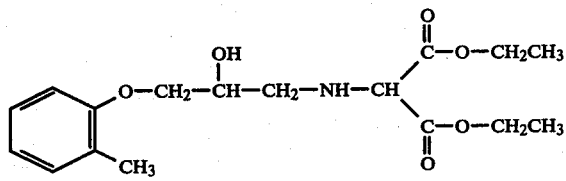

except 1-(2,3-epoxypropoxy)naphthalene was substituted for 2,3-epoxypropoxybenzene, 3-aminopropionic acid was substituted for 4-aminobutyric acid, and methanol was substituted for ethanol in the esterification step. The product was crystallized in 10% yield as its oxalate salt and had a melting point of 180° C. The NMR spectrum and elemental analysis were consistent with the assigned structure.

EXAMPLE XXX

This example describes procedures for the preparation of a compound of the formula (structure shown)

Diethyl 2-Amino-[N-[2-Hydroxy-3-(2-methylphenoxy)propyl]]-propanedioate Hydrochloride A mixture of 10 g (0.061 mole) of 2-methyl-1-(2,3-epoxypropoxy)benzene, 12.9 gm (0.061 mole) of diethylaminomalonate hydrochloride and 6.2 gm (0.061 mole) of triethylamine in 100 mL of ethanol was heated to reflux for 24 hours. The reaction medium was then evaporated under reduced pressure and the residue treated with ether. The solid triethylamine hydrochloride side product was then removed by filtration. The mother liquor was then treated with HCl gas and provided 2.7 (12%) of white crystals: mp 105°–6°. The NMR spectrum was consistent with the assigned structure, and the elemental analysis was consistent with the formula C₁₇H₂₆NC2O₆.

EXAMPLE XXXI

This example describes procedures for the preparation of a compound of the formula:

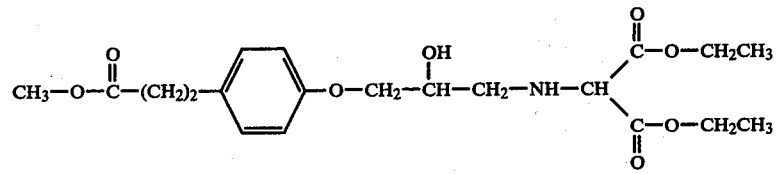

Diethyl 2-Amino-[N-[2-hydroxy-3-(4-(2-carbomethoxyethyl)-phenoxypropyl]]propanedioate Hydrochloride A mixture of 11.8 gm (0.05 mole) of methyl 3-[4-(2,3-epoxypropoxy)phenyl]propionate, 10.6 gm (0.05 mole) of diethyl 2-aminomalonate hydrochloride and 7 mL (0.05 mole) of diethyl 2-aminomalonate hydrochloride and 7 mL (0.05 mole) of triethylamine in 100 mL of isopropanol was heated to reflux for 4 hours. The reaction medium was then filtered and evaporated under vacuum. The resulting oil was taken up in 100 mL toluene and washed with 3×50 mL water. The organic phase was then dried over MgSO₄ and evaporated under vacuum. The free amine oil was taken up in ethanol and converted to its hydrochloride salt by adding ethereal HCl. Approximately 4 gm (20%) of white crystals were obtained: mp 144°–145°. The NMR spectrum was consistent with the assigned structure and the elemental analysis was consistent with the formula C₂₀H₃₀NO₈Cl.

EXAMPLES XXXII–LIX

Several of the compounds of the present invention were tested for β-blocking activity in vitro using guinea pig right atria and guinea pig tracheal strips mounted in a tissue bath containing oxygenated (95% O₂-5% CO₂) Krebs physiological salt solution at 37° C. Each tissue was suspended between a fixed glass rod and a Statham ® Universal Transducer connected to a Beckman ® recorder. Atria were allowed to beat spontaneously under a loading tension of approximately 0.5 gm. Intrinsic depressant for stimulant activity was determined for each compound by progressively increasing concentrations in the tissue baths at 60-minute intervals. Tissues were not washed between increments. The maximum concentration showing little or no cardiodepressant activity was chosen for blockade experiments. Changes in rate in response to isoproterenol were measured in the absence and presence of test compounds. Spiral strips of guinea pig trachea were suspended under 5 gm resting tension and incubated with phentolamine, tropolone and cocaine. Active tension was generated by addition of carbachol ($3.0 \times 10^{-7}$ M) and decreases in tension in response to isoproterenol were quantitated. Cumulative concentration-response curves were produced with isoproterenol both before and after 60 minute incubation of test compounds with atria and trachea. The blocking potency of test compounds was estimated by computing $pA_2$ values ($-\log K_B$) by the method of Furchgott, The Pharmacological Differentiation of Adrenergic Receptors, *Ann. N.Y. Acad. Sci.;* 139: 553–570 (1967). Comparison of blockade of right atrial and tracheal responses to isoproterenol permitted assessment of cardioselectivity of test compounds; i.e., cardioselective compounds are relatively more effective in blocking atrial rate than tracheal force responses to isoproterenol. The degree of cardioselectivity was estimated from the ratio, $K_B$ tracheal/$K_B$ atrial ($10^{(pA2atria - pA2trachea)}$). A ratio greater than one indicates cardioselectivity. Test drugs were dissolved in distilled water and added to the bath (30 mL) in a volume of 10 or 100 μL. The results of the in vitro tests are contained in Table IV. All of the test compounds were active β-blockers.

EXAMPLES LX–LXXIV

The duration of β-blockade was determined in vivo using pentobartital-anesthetized dogs instrumented for measurement of heart rate using a Beckman ® cardiotachometer triggered electronically by a phasic aortic blood pressure signal. Both vagus nerves were severed in the cervical region and the animals were mechanically ventilated. Two experimental designs were used. The first employed a 40-minute infusion of test compound and the second used a 3-hour infusion of test compound. In the 40-minute model, isoproterenol was infused into a foreleg vein at the rate of 0.5 μg/kg/min to induce a β-receptor mediated tachycardia. Various doses of test compound are then infused into a femoral vein over a period of 40 minutes. This infusion was then terminated and recovery from blockade was quantitated. The percent inhibition of the heart rate response to isoproterenol after 40 minutes of infusion of the test compound was computed along with the total cumulative doses received over the 40-minute period. This cumulative dose is expressed as mg/kg and is an indication of potency. The time period required for 80% recovery of heart rate response for each dose of test drug was also measured to quantitate duration of action. To facilitate comparison of data between animals, the data for potency and duration of action were normalized to a level of 50% inhibition of the isoproterenol response via least squares regression of data from each animal. Test compounds were dissolved in 0.9% NaCl and infused at a rate of 0.05 mL/kg/min or less. In the 3-hour infusion model, bolus doses of isoproterenol (0.4 μg/kg) were used to assess the degree of β-blockade and recovery from β-blockade after termination of the infusion. The doses were spaced at 10-minute intervals and were given before, during and following the infusion of test compounds. The infusion rate was adjusted so that at the end of the 3-hour infusion period the degree of isoproterenol inhibition averaged about 50% of control. The results of isoproterenol inhibition averaged about 50% of control. The results of the 40-minute infusion are shown in Table V, and the results of the 3-hour infusion are shown in Table VI.

EXAMPLE LXXV–LXXXII

These examples describe experiments which demonstrate the disappearance of the compounds of the present invention in vitro in human whole blood, dog whole blood, and dog liver homogenate. The rate of disappearance of a compound is expressed as the half-life ($T_{\frac{1}{2}}$), which is the time period in which one-half of the initial amount of compound tested disappears. In each experiment, 1 mL of a solution containing 50 μg of the test compound was added to 1 mL of whole blood or 1 mL of a 33% (w/v) liver homogenate. The samples were incubated in a Dubnoff shaking metabolic incubator for 2.5, 5.0, 10.0, 20.0, 30.0 and 60.0 minutes at 37° C. At the designated time periods, the test mixtures were removed from the incubator and transferred to a 0° C. ice bath. Acetonitrile (2 mL) was immediately added and the mixtures were mixed to stop enzymatic hydrolysis. Zero time samples were prepared by adding 2 mL of acetonrile to denature the proteins prior to addition of the test compounds. After centrifugation to sediment denatured proteins, 2 mL of the supernatant was removed and analyzed by high pressure liquid chromatography, using a mobile phase of 60% acetonitrile/40% 0.5M sodium phosphate buffer (pH 6.6), a U.V. detector and Waters ® μBondapak Phenyl column. The half life of each test compound was determined graphically by plotting the decrease in concentration as a function of time. The results of the experiments are shown in Table VII.

TABLE IV

| Example | Test Compound (Numerical Designation Indicates Previous Example Which Describes Preparation of Compound) | $pA_2$ Atria | $pA_2$ Trachea | Cardioselectivity |
|---|---|---|---|---|
| XXXII | I | 5.7 | 5.6 | 1 |
| XXXIII | II | 6.2 | 6.2 | 1 |
| XXXIV | III | 7.3 | 5.9 | 25 |
| XXXV | IV | 6.6 | 6.0 | 4 |
| XXXVI | V | inactive | inactive | — |
| XXXVII | VI | 6.4 | 5.6 | 6 |
| XXXVIII | VII | 5.9 | <5.0 | >8 |
| XXXIX | VIII | 6.6 | 6.6 | 1.0 |
| XL | X | 7.5 | 7.4 | 1 |

TABLE IV-continued

| Example | Test Compound (Numerical Designation Indicates Previous Example Which Describes Preparation of Compound) | pA$_2$ Atria | Trachea | Cardioselectivity |
|---|---|---|---|---|
| XLI | XI | 7.4 | 6.7 | 5 |
| XLII | XII | 7.8 | 7.4 | 2.5 |
| XLIII | XIII | 5.1 | — | — |
| XLIV | XIV | 5.2 | — | — |
| XLV | XV | 6.6 | 5.9 | 5 |
| XLVI | XVI | 6.9 | 6.7 | 1.6 |
| XLVII | XVII | 7.5 | 7.0 | 1.6 |
| XLVIII | XVIII | 6.4 | — | — |
| XLIX | XIX | 5.7 | — | — |
| L | XX | 5.7 | — | — |
| LI | XXI | 7.4 | 6.6 | 6 |
| LII | XXII | 7.4 | 6.7 | 5 |
| LIII | XXIII | 6.7 | 6.5 | 1.6 |
| LIV | XXIV | 6.4 | 6.7 | .5 |
| LV | XXV | 5.8 | 4.9 | 8 |
| LVI | XXVI | 6.1 | — | — |
| LVII | XXVII | 5.9 | 6.2 | 0.5 |
| LVIII | XXVIII | 7.0 | 6.6 | 2.5 |
| LIX | XXIX | 7.1 | 7.6 | 0.3 |
| Propranolol | | 8.7 | 8.9 | 0.6 |
| Practolol | | 6.6 | 5.8 | 6.0 |

TABLE V

| Example | Test Compound (Numerical Designation Indicates Previous Example Which Describes Preparation of Compound | Potency (mg/kg/40 min) | 80% Recovery Time (minutes) | No. of Experiments |
|---|---|---|---|---|
| LX | I | very low | — | 4 |
| LXI | II | — | 53 ± 11 | — |
| LXII | III | 12.6 ± 4.1 | 29 ± 13 | 4 |
| LXIII | IV | 16.9 ± 9.1 | 17 ± 4 | 3 |
| LXIV | XXV | 17.2 ± 1.2 | 11 ± 2 | 4 |
| LXV | X | 0.99 ± 0.27 | 14 ± 2 | 5 |
| LXVI | XI | 3.1 ± 0.7 | 15 ± 2 | 4 |
| LXVII | XII | 6.8 ± 3.7 | 11 ± 2 | 3 |
| Propranolol | | | 46 | |
| Practolol | | | 61 | |

TABLE VI

| Example | Test Compound (Numerical Designation Indicates Previous Example Which Describes Preparation of Compound | Potency (mg/kg/ 180 min) | % I* | 80% Recovery Time (minutes) | No. of Experiments |
|---|---|---|---|---|---|
| LXVIII | XVII | 4.4 | 56 ± 4 | 27 ± 4 | 4 |
| LXIX | VIII | 27.4 ± 6.0 | 53 ± 2 | 10 ± 2 | 5 |
| LXX | XXVIII | 167.7 | 85 | >60 | 1 |
| LXXI | X | 6.8 | 69 ± 5 | >60 | 3 |
| LXXII | XXII | 8.5 | 77 | >60 | 3 |
| LXXIII | XXI | 10.9 | 77 | >60 | 2 |
| LXXIV | XVIII | 54 ± 14 | 54 ± 8 | >60 | 3 |
| Propranolol | | | | No appreciable recovery after several hours | |
| Practolol | | | | No appreciable recovery after several hours | |

*Percent inhibition of heart rate response to isoproterenol

TABLE VII

| Example | Test Compound* | Human Whole Blood T½ (Minutes) | Dog Whole Blood T½ (Minutes) | Dog Liver Homogenate |
|---|---|---|---|---|
| LXXV | XII | 93 ± 30 | 152 ± 71 | 8.8 ± 6 |
| LXXVI | XI | 117 ± 39 | >180 | — |
| LXXVII | XXII | 118 ± 26 | 40 ± 15 | 3 ± 3 |
| LXXVIII | XXI | 127 ± 50 | 74 ± 21 | 4 ± 3 |
| LXXIX | XVII | 148 ± 2 | 52 ± 9 | 9 ± 8 |
| LXXX | X | 155 ± 9 | 180 ± 0 | 3 ± 1 |
| LXXXI | XXV | 158 ± 8 | >180 | 4 ± 2.5 |
| LXXXII | XV | >180 | >180 | 9 ± 6 |

*Numerical Designation Indicates Previous Example which Describes Preparation of Compound

We claim:

1. A method for the treatment or prophylaxis of cardiac disorders in a mammal, comprising administering by intravenous infusion into a mammal having a critical cardiac illness a β-blocking ester compound of the formula

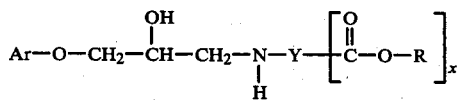

wherein Y is a straight or branched carbon chain of from 1 to about 10 carbon atoms or aralkyl of from 8 to about 20 carbon atoms; R is lower alkyl, lower alkenyl, lower alkynyl, aryl or aralkyl; x is an integer from 1 to about 3, provided that when x is greater than 1, different occurrences of the —COOR group may be the same or different; Ar is phenyl or naphthyl, optionally additionally substituted with lower alkyl, lower alkenyl, lower alkynyl, lower alkoxy, halogen, acetamido, amino, nitro, lower alkylamino, hydroxy, lower hydroxyalkyl, cyano or a group of the formula

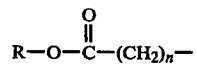

wherein n is an integer from 0 to about 10 and R is as defined above; or a pharmaceutically acceptable salt thereof; which β-blocking ester compound rapidly converts to inactive metabolites upon in vivo enzymatic cleavage; wherein said β-blocking ester compound is intravenously infused at a rate sufficient to establish an effective β-blockade in said mammal, and said infusion is then terminated to effect substantial recovery of said mammal from the β-blocking effects of said compound.

2. The method of claim 1 wherein R is lower alkyl of from 1 to about 10 carbon atoms, lower alkenyl of from 2 to about 10 carbon atoms, lower alkynyl of from 2 to about 10 carbon atoms, aryl of from 6 to about 10 carbon atoms, or aralkyl, wherein the alkyl portion contains from 1 to about 10 carbon atoms and the aryl portion contains from 6 to about 10 carbon atoms.

3. The method of claim 1, wherein Y is a straight or branched carbon chain of from 1 to about 6 carbon atoms or aralkyl of from 8 to about 12 carbon atoms, and R is lower alkyl of from 1 to about 5 carbon atoms, lower alkenyl of from 2 to about 5 carbon atoms, lower alkynyl of from 2 to about 5 carbon atoms, or aralkyl wherein the alkyl portion contains from 1 to about 5 carbon atoms and the aryl portion contains from 6 to about 10 carbon atoms.

4. The method of claim 3, wherein Ar is optionally substituted with lower alkyl of from 1 to about 5 carbon atoms, lower alkenyl of from 2 to about 5 carbon atoms, lower alkynyl of from 2 to about 5 carbon atoms, lower alkoxy of from 1 to about 5 carbon atoms, fluoro, chloro, acetamido, amino, nitro, lower alkylamino of from 1 to about 5 carbon atoms, hydroxy, lower hydroxyalkyl of from 1 to about 5 carbon atoms, cyano, or a group of the formula

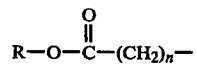

wherein n is an integer from 0 to about 5 and R is as defined above.

5. The method of claim 4, wherein Y is a straight or branched carbon chain of from 1 to about 4 carbon atoms and R is lower alkyl of from 1 to about 4 carbon atoms, aryl, of from 6 to about 8 carbon atoms or aralkyl, wherein the alkyl portions contain from 1 to about 4 carbon atoms and the aryl portion contains from 6 to about 8 carbon atoms, and x is 1 or 2.

6. The method of claim 5, wherein Ar is phenyl, optionally substituted with lower alkyl of from 1 to about 5 carbon atoms, fluoro, chloro, nitro or a group of the formula

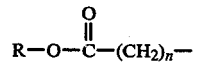

wherein n is an integer from 0 to about 5, R is as defined above, and x is 1.

7. The method of claim 5, wherein Ar is 2-methylphenyl.

8. The method of claim 7, wherein R is methyl or ethyl.

9. The method of claim 1, wherein the compound is of the formula

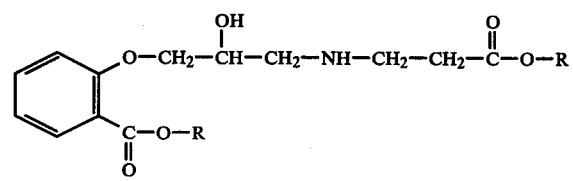

wherein R is methyl or ethyl, or a pharmaceutically acceptable salt thereof.

10. The method of claim 1, 2, 4, 5, 7, 8 or 9, wherein said compound is the hydrochloride, sulfate, phosphate, gluconate or tartrate acid addition salt.

11. The method of claim 1, 2, 4, 5, 7, 8 or 9, wherein said β-blocking ester compound is intravenously infused at a rate of from about 0.001 to about 100 mg. of compound per kg. of body weight of said mammal per hour.

12. The method of claim 1, wherein following termination of infusion, the β-blocking effects of said compound in said mammal are reduced by at least 50% within about one hour.

13. The method of claim 11, wherein following termination of infusion, the β-blocking effects of said compound in said mammal are reduced by at least 50% within about 15 minutes.

14. A compound of the formula

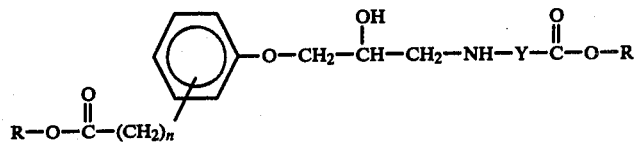

wherein Y is a straight or branched carbon chain of from 1 to about 10 carbon atoms or aralkyl of from 8 to about 20 carbon atoms; R is lower alkyl of from 1 to about 10 carbon atoms, lower alkenyl of from 2 to about 10 carbon atoms, lower alkynyl of from 2 to about 10 carbon atoms, aryl of from 6 to about 10 carbon atoms or aralkyl, wherein the alkyl portion contains from 1 to about 10 carbon atoms and the aryl portion contains from 6 to about 10 carbon atoms; the

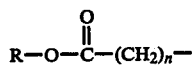

group is in the ortho or para position on the phenyl ring with respect to the amine-containing side chain; n is an integer from 0 to about 2; or a pharmaceutically acceptable salt thereof.

15. The compound of claim 14, wherein Y is a straight or branched carbon chain of from 1 to about 6 carbon atoms or aralkyl of from 8 to about 12 carbon atoms; R is lower alkyl of from 1 to about 5 carbon atoms, lower alkenyl of from 2 to about 5 carbon atoms, lower alkynyl of from 2 to about 5 carbon atoms; or a pharmaceutically acceptable salt thereof.

16. The compound of claim 14, wherein Y is a straight or branched carbon chain of from 1 to about 4 carbon atoms; R is lower alkyl of from 1 to about 4 carbon atoms; or a pharmaceutically acceptable salt thereof.

17. The compound of claim 14, wherein Y is methylene or ethylene and R is methyl or ethyl; or a pharmaceutically acceptable salt thereof.

18. The compound of claim 17 wherein the

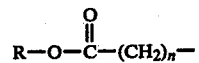

group is in the ortho position on the phenyl ring with respect to the amine-containing side chain, and n is 0.

19. The compound of the formula

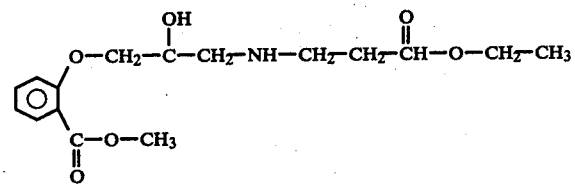

or a pharmaceutically acceptable salt thereof.

20. The compound of claim 14, 15, 16, 17, 18 or 19 as the hydrochloride, sulfate, phosphate, gluconate or tartrate acid addition salt.

* * * * *

UNITED STATES PATENT AND TRADEMARK OFFICE
CERTIFICATE OF CORRECTION

PATENT NO. : 4,450,173

DATED : May 22, 1984

INVENTOR(S) : Erhardt et al.

Page 1 of 2

It is certified that error appears in the above-identified patent and that said Letters Patent is hereby corrected as shown below: Title page item [75]

Inventors should include John P. O'Donnell, Morgantown, West Virginia

Column 5, line 38, "B0.01" should be "0.01".

Column 12, line 33, "subjected" should be "substituted".

Column 13, Table II, line 47, and column 14, line 4,

"Ar-O-CH$_2$-CH(OH)-CH$_2$CH$_2$-NH-CH$_2$-CH$_2$-C(=O)-O-CH$_2$CH$_3$" should be "Ar-O-CH$_2$-CH(OH)-CH$_2$-NH-CH$_2$-CH$_2$-C(=O)-O-CH$_2$CH$_3$".

UNITED STATES PATENT AND TRADEMARK OFFICE
CERTIFICATE OF CORRECTION

PATENT NO. : 4,450,173
DATED : May 22, 1984
INVENTOR(S) : Erhardt, et al.

It is certified that error appears in the above-identified patent and that said Letters Patent is hereby corrected as shown below:

Column 15, Table III, the circle is missing from the ring.

Claim 19, line 25, should be 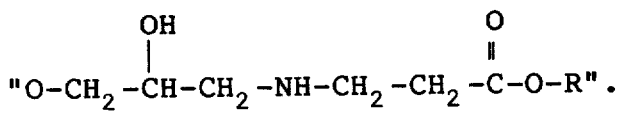

Signed and Sealed this

Thirtieth Day of April 1985

[SEAL]

Attest:

DONALD J. QUIGG

Attesting Officer      Acting Commissioner of Patents and Trademarks